(12) United States Patent
Palumbo et al.

(10) Patent No.: US 6,232,250 B1
(45) Date of Patent: May 15, 2001

(54) ABSORBENT ARTICLE

(75) Inventors: Gianfranco Palumbo, Pescara; Antonio d'Ambrosio, *deceased*, late of Pescara, by Anna Perfetti d'Ambrosio, legal representative; Giovanni Carlucci, Chieti, all of (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/553,706

(22) PCT Filed: Jun. 3, 1994

(86) PCT No.: PCT/EP94/01814

§ 371 Date: Aug. 7, 1997

§ 102(e) Date: Aug. 7, 1997

(87) PCT Pub. No.: WO94/28838

PCT Pub. Date: Dec. 22, 1994

(Under 37 CFR 1.47)

(30) Foreign Application Priority Data

Jun. 4, 1993 (IT) ................................................ T093A0402

(51) Int. Cl.[7] ................................ B32B 5/08; B32B 5/12
(52) U.S. Cl. ....................... 442/389; 604/368; 604/378; 442/389; 442/414; 442/415; 428/156; 428/171; 428/913
(58) Field of Search .................................... 604/378, 368; 428/913, 156, 171; 442/389, 414, 415

(56) References Cited

U.S. PATENT DOCUMENTS

| | | | |
|---|---|---|---|
| 3,881,489 | 5/1975 | Hartwell | 604/369 |
| 3,929,135 | 12/1975 | Thompson | 604/385.1 |
| 3,989,867 | 11/1976 | Sisson | 428/132 |
| 4,578,414 | 3/1986 | Sawyer et al. | 524/310 |
| 4,761,258 * | 8/1988 | Enloe | 264/518 |
| 4,904,249 * | 2/1990 | Miller et al. | 604/378 |
| 5,147,343 * | 9/1992 | Kellenberger | 604/368 |
| 5,364,382 * | 11/1994 | Latimer et al. | 604/378 |
| 5,429,629 * | 7/1995 | Latimer et al. | 604/378 |
| 5,591,149 * | 1/1997 | Cree et al. | 604/378 |
| 5,913,850 * | 6/1999 | D'Alessio | 604/378 |

FOREIGN PATENT DOCUMENTS

| | | |
|---|---|---|
| 0 018 020 | 10/1980 | (EP) . |
| 0 018 684 | 11/1980 | (EP) . |
| 0 059 506 | 9/1982 | (EP) . |
| 108637 | 5/1984 | (EP) . |
| 0 207 904 | 1/1987 | (EP) . |
| 306262 | 3/1989 | (EP) . |
| 532005 | 3/1993 | (EP) . |
| WO 9111165 | 8/1991 | (WO) . |
| WO91/14733 | 10/1991 | (WO) . |
| WO91/14734 | 10/1991 | (WO) . |
| WO91/15362 | 10/1991 | (WO) . |
| WO91/15368 | 10/1991 | (WO) . |
| WO93/03699 | 3/1993 | (WO) . |
| WO93/04092 | 3/1993 | (WO) . |
| WO93/04093 | 3/1993 | (WO) . |
| WO93/04113 | 3/1993 | (WO) . |
| WO93/04115 | 3/1993 | (WO) . |
| WO94/26834 | 11/1994 | (WO) . |

* cited by examiner

*Primary Examiner*—Terrel Morris
*Assistant Examiner*—John J. Guarriello
(74) *Attorney, Agent, or Firm*—McDermott, Will & Emery

(57) ABSTRACT

An article for absorbing fluid includes a fluid-storage region and a fluid receiving region. The fluid receiving region releases fluid to the fluid storage and has a dry laid web of staple fibers with a high bulkiness. The article may be used for treating female incontinence.

33 Claims, 1 Drawing Sheet

ABSORBENT ARTICLE

Figure 1:
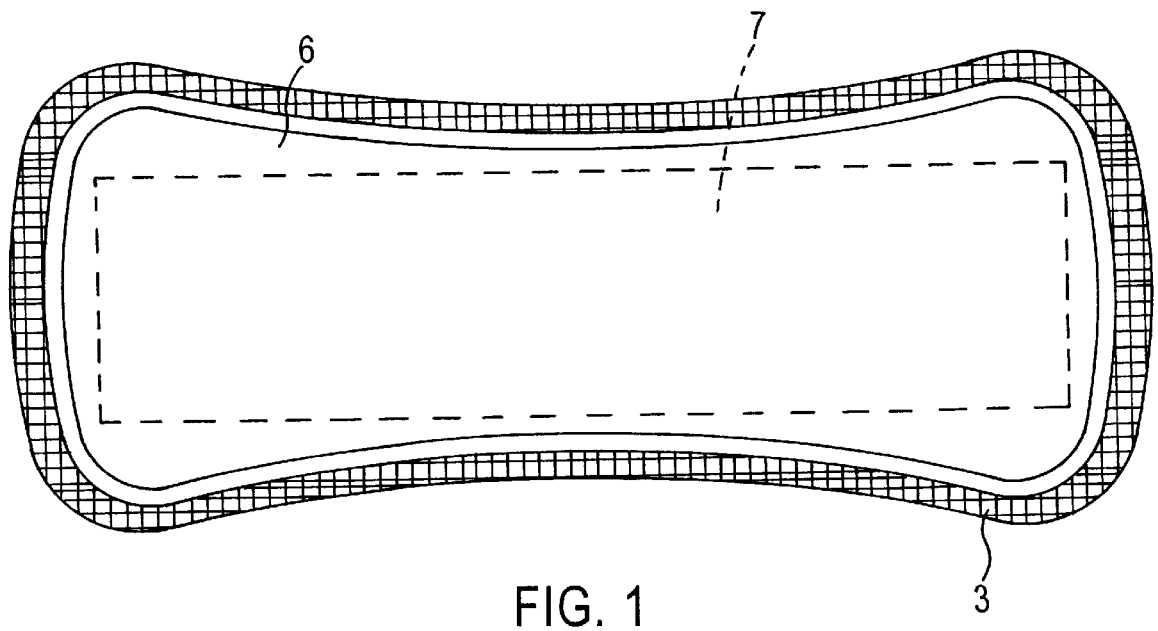

This invention relates to an absorbent article. It is particularly concerned with an absorbent article, for example in the form of a pad, which can be used by women suffering from light and moderate incontinence. The invention will be so described below. However, the invention is of more general applicability in relation to the absorption of body fluids, either urine or menstrua. It can therefore be used, for example, in the manufacture of infant diapers, and in incontinence products for adults, in addition to the incontinence product specifically identified above.

A condition of light incontinence exists in many women. An absorbent pad, or other article, for use by those with this condition should desirably (a) Be thin, and with a shape fitting well into the underpants, to provide discretion when worn under normal clothing.

(b) Be absorbent enough to handle large quantities of urine.

(c) Absorb rapidly enough to accept the surge of urine (gush handling) that can occur from women who have this condition, and maintain this capability even through multiple gushes.

Research indicates that 10–20% of the female population suffer from light involuntary urine losses. The magnitude of the problem varies from losing just a few dribbles in special situations (coughing, sneezing, during sports) to a more serious, permanent problem (after menopause or in conjunction with gynaecological operations). The product selected by such women, and the usage frequency, depends on the seriousness of the problem: pantiliner usage with 1–2 changes per day for occasional urine losses moving to a higher change frequency (2–8 pantiliners/day) for higher loadings and/or more frequent bladder weakness. For those at the upper end of the problem range, pantiliners are not sufficiently absorbent, besides being prone to bunching and to disintegration during use, and such women use 2–3 catamenial pads per day.

Existing products for light incontinence are similar to oversized thick catamenial pads. Most are very thick, about 15 mm thick, and this does not provide the degree of discretion the user desires. Furthermore, these products have absorbent cores that typically collapse when wetted, thus making them deficient in fluid absorption rate for subsequent loadings.

For the lightest conditions of light incontinence, many women use standard pantiliners. These products provide the desired level of discretion under clothing; however, they are totally inadequate in absorbency. Part of this deficiency is in absorbent capacity, but more important is the deficiency in absorbent rate.

One object of the present invention is to provide an absorbent article for dealing with light and moderate incontinence, which is discrete, has the absorbent capacity required, and has the necessary gush handling ability.

According to one aspect of the present invention there is provided an article for absorbing fluid, which comprises a fluid-storage region and a fluid-receiving region adapted to release fluid to the fluid-storage region, the fluid-receiving region being formed of a dry laid, for example an airlaid, web of staple fibers, the web having a bulkiness, as measured under a pressure of 2 kPa, of at least 15 cm$^3$/g.

By "staple fibers" we mean fibers which are not continuous, and which may be synthetic fibers, natural fibers, or a mixture of synthetic and natural fibers.

It is believed that the high bulkiness of the fluid-receiving region is such that the fluid is free to flow with very little impedance by the fibers defining the region. This is in contrast to the approach adopted in known products dealing with incontinence, where any fluid-receiving region serves as a wick to transfer fluid received at one part of the region to other parts thereof. However, it is to be understood that this explanation is offered here as a suggestion only, and no categorical assertion is made that it is correct.

Preferred features of the fluid-receiving and fluid-storage regions are described below and are set out in the subclaims.

The article preferably further comprises a water-permeable top sheet in face-to-face relationship with the said fluid-receiving sheet, on the opposite side thereof to the fluid-storage sheet, and a water-impermeable backsheet in face-to-face relationship with the fluid-storage sheet, on the opposite side thereof to the fluid-receiving sheet.

The topsheet and backsheet are preferably sealed to one another, and the article shaped to form a pad suitable for incontinent females.

According to another aspect of the invention there is provided an absorbent pad for use by a user suffering from incontinence, which comprises a fluid-storage layer, and a fluid-receiving layer adapted to receive fluid from the user and release it to the fluid-storage layer, the pad having a thickness when dry of t mm, as measured with the pad under pressure of 2 kPa, a fluid storage capacity of s ml and the ability to receive gushes at an average rate, as measured over three successive equal gushes totalling G (ml), of up to g ml/sec, where $s/t \geq 8$ ml/mm; and $g/t \geq 0.1$ ml/mm. sec;

at least for some value of $G/s \geq 2/3$.

Preferably $g/t \geq 0.2$ ml/mm. sec., more preferably $\geq 0.3$ ml/mm/sec.

According to yet another aspect of the invention there is provided an article for absorbing fluid, which comprises a fluid-storage region, a fluid-receiving region adapted to release fluid to the fluid-storage region, a fluid-permeable topsheet in face-to-face relationship with the said fluid-receiving sheet, on the opposite side thereof to the fluid-storage sheet, and a fluid-impermeable backsheet in face-to-face relationship with the fluid-storage sheet, on the opposite side thereof to the fluid-receiving sheet, the article having a thickness, when dry, of $t_d$, and a thickness, when wetted to its maximum extent, of $t_w$, with $t_w > t_d$, the topsheet and backsheet being sealed together along respective edge portions thereof, and the topsheet having a fluid permeable central area, and a fluid impermeable area adjacent the sealed edge portion thereof, the size of the fluid impermeable area being such that, even when the article is wet to its maximum extent, the fluid permeable area of the sheet is not in communication with at least a major part of the edges of the fluid-receiving region.

The absorbent article can be thin, being as little as 3 mm in thickness, or even less, and provided it has the correct contours to fit well into underwear can be highly discreet. The key is that the article swells only when heavily wetted. This is in contrast to existing products on the market, which if they provide anything approaching an acceptable level of absorbence, are bulky even when dry.

Figure 2:
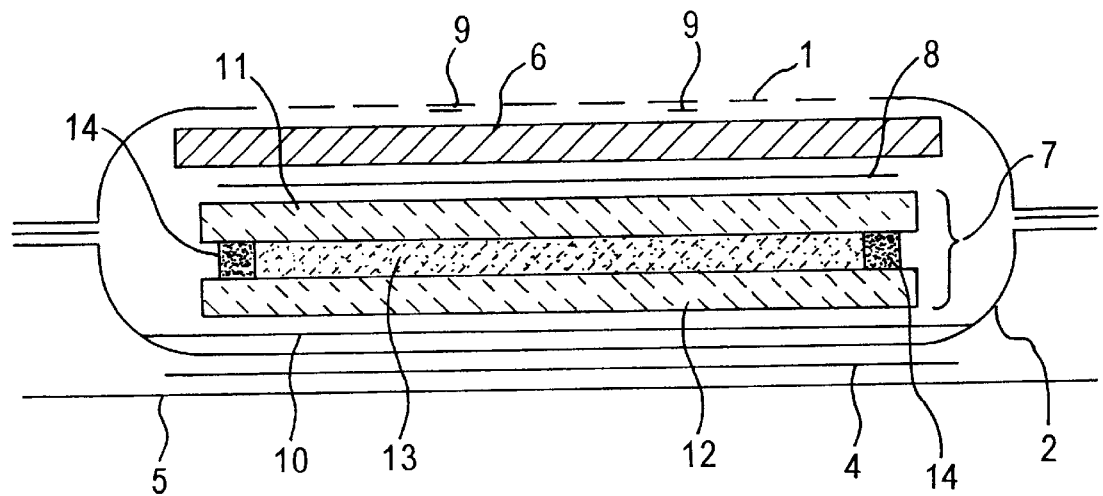

In the accompanying drawings:

FIG. 1 is a plan view of an embodiment of an absorbent article according to the present invention; and FIG. 2 is a diagrammatic cross-section, on a larger scale, through the crotch region of the article shown in FIG. 1.

The embodiment of FIGS. 1 and 2 comprises a liquid permeable topsheet 1 and a liquid impermeable backsheet 2 sealed to one another along a peripheral region 3 thereof by, for example, thermal bonding. The backsheet 2 has a layer 4 of hot-melt adhesive coated thereon, to which is attached a release sheet 5 which is removed by the user before use. Within the enclosure defined by the topsheet 1 and backsheet 2 there is provided a secondary sheet 6, adjacent to topsheet 1, and an absorbent storage core 7. The sheet 6 and core 7 are attached to one another by a layer 8 of cold glue. The layer 8 is discontinuous, so that liquid can pass from the sheet 6 to the core 7.

The layer 8 is preferably of the type disclosed in our copending Italian Patent Application No. T093A 000338 filed on May 17, 1993 and entitled "Adhesive composition, related methods and use". The copending application describes a water-based adhesive composition comprising a blend of adhesive polymers in an aqueous system, characterised in that the blend of adhesive polymers is:

20–60% by weight of an acrylic polymer having a polarity balance expressed as water absorption according to DIN 53495 of 3 to 20%; and correspondingly 40–80% by weight of a compatible tackifying resin having a degree of hydrophobicity measured as the contact angle between a dried film of the resin and a drop of distilled water of not less than 60°;

the percentages being based on the total of acrylic polymer plus tackifying resin expressed as dry solids.

The layer 6 is attached to the topsheet 1 by a plurality of narrow stripes 9 of hot-melt adhesive. The core 7 is attached to the backsheet 2 by a layer 10 of hot melt adhesive.

It can be seen that the core 7 consists of three layers, namely upper and lower layers 11 and 12 each of a cellulose-based material, and a middle layer 13 of a water-insoluble hydrogel material. At the edges of the layer 13 are lines of adhesive 14 which serve to confine the hydrogel material and prevent liquid therein leaking out.

The absorbent article will now be described in more detail with reference to the four layers thereof.

1. Topsheet

The top layer (user side) is a topsheet that must be comfortable to the touch, provide a dry feeling over an absorbent core filled with liquid, and pass fluid rapidly into the interior of the core. It is liquid permeable in the central longitudinal zone and is liquid impermeable at least in the two lateral zones in order to handle totally the urine during the gush, while avoiding lateral leakage. The width of the liquid impermeable area is such that even when the article is wet to its maximum extent, and is correspondingly swollen, the fluid permeable area of the sheet is not in communication with the lateral edges of the fluid-receiving secondary sheet. This avoid lateral leakage from the core. The liquid impermeable area may extend completely around the liquid permeable area.

This element can be of a variety of known materials, for example: a) a formed-film topsheet as described in U.S. Pat. No. 3,929,135, or any of European Patent specifications Nos. EP-A-0018020, EP-A-0018684 and EP-A-0059506, (b) a partially perforated fiber/film composite described in EP-A-207904, the perforated area thereof providing a liquid permeable area, and the unperforated area thereof providing a liquid impermeable area, or (c) a nonwoven film produced by the spunbonding or by a carded, thermal-bonded process, or a sheet produced by various other processes currently practised.

2. Secondary Sheet

This element has the characteristics of accepting a high rate of fluid intake, serving as a temporary reservoir for the fluid, and then draining substantially completely into the storage core in order to remain empty for subsequent fluid loadings. In addition, this element must resist collapse when wet so that it maintains its performance through multiple loadings. This element must do all these things while also remaining extremely thin. An airlaid web of synthetic fibres can be used for this purpose. The secondary sheet should preferably have hydrophilic properties.

The secondary sheet preferably has the following characteristics:

(a) A thickness of from 1 to 10 mm, more preferably from 1.5 to 6 mm, still more preferably from 1.7 to 4.5 mm, and even more preferably from 2 to 4 mm, the thickness being measured with the sheet under a pressure of 2 kPa.

(b) A basis weight of from 35 to 300 g/m$^2$, more preferably from in excess of 40 up to 40 to 200 g/m$^2$, still more preferably from 42 or 43 to 200 g/m$^2$, and yet more preferably from 50 to 180 g/m$^2$. Typically, it may be up to 150 cm$^3$/g. For example, basis weights of 45, 60, 80 and 120 g/m$^2$ have been used and found to be satisfactory.

(c) As already mentioned, the sheet has a bulkiness of at least 15 cm$^3$/g, when the sheet is under a pressure of 2 kPa. More preferably, the bulkiness is from 15 to 65 cm$^3$/g, still more preferably from 20 to 60 cm$^3$/g, and yet more preferably from 25 to 55 cm$^3$/g. It may advantageously be from 30 to 50 cm$^3$/g. Desirably, the minimum value for the bulkiness is 32, 33, 34 or 35 cm$^3$/g.

(d) The ability to discharge to the storage core at least 95%, and more preferably at least 99% of the fluid which it receives in a loading.

(e) A wet collapse at 2.7 kPa of not more than 45%, and more preferably not more than 40%.

(f) A wet resilience at 0.1 kPa of not more than 40%, more preferably not more than 30%, and still more preferably not more than 25%.

(g) A wetting time of not more than 5 seconds, and preferably not more than 2 seconds.

(h) It is formed of fibres having a diameter of not more than 40 μm, preferably not more than 20 μm, and still more preferably from 15–20 μm, and a length of not more than 20 mm, preferably not more than 12 mm, and most preferably about 6 mm.

3. Storage Core

The third layer is a thin, high-capacity absorbent core. While thin when dry, this element of the structure preferably expands when wetted to provide a high, tenacious fluid-holding ability, and it must avoid collapse when wet. The storage core is itself preferably formed of a plurality of layers. For example, a three layer structure may be used in which the outer layers are of a cellulose tissue material (and may be the same as, or different from, one another). The middle layer is of a water-insoluble hydrogel, which is a polymeric material in particulate form, capable of absorbing a large quantity of liquid and retaining it under moderate pressures.

It is important that the secondary sheet and the storage core work together. In particular, given the form of secondary sheet used herein, it is possible in this structure to avoid the typical problem of gel blocking in the storage core, because the secondary sheet provides total distribution of the fluid, and then drains it into the storage core whenever the storage core has not yet received fluid.

As an alternative to the form of storage core described above, it can be one of a number of thin, high-capacity materials. For example, the storage core can be a sheet of fused AGM particles as described in International Patent Applications Nos. WO91/14733, WO91/14734, WO91/15362 and WO91/15368 or a high capacity foam, as described, for example, in International Patent Publications Nos. WO93/04092, WO93/03699, WO93/04093, WO93/04113 and WO93/04115.

4. Impervious Backsheet

The backsheet is impervious to liquids and, thus, prevents fluid which may be expressed from absorbent core from soiling the body or clothing of the user. Suitable materials are well known in the art, including woven and nonwoven fabrics which have been treated to render them liquid repellent. Breathable or vapour pervious, liquid resistant materials, and those materials described in U.S. Pat. No. 3,881,489 and U.S. Pat. No. 3,989,867 can also be used. Preferred materials are those materials that are fluid and vapour impervious, because they provide additional fluid strikethrough protection. Especially preferred materials include formed thermoplastic films.

EXAMPLE 1

The topsheet is partially perforated fiber/film composite coverstock of the type described in EP-A-0207904. It is partially perforated over a rectangular area which runs lengthwise and centrally of the pad and which has a width of 38 mm.

The secondary sheet is formed using a hydrophilic resin from Dow Chemical called ASPUN (CODE XU 61518.11) which is a polyethylene resin containing a wetting agent, of the type described in U.S. Pat. No. 4,578,414. Polyethylene itself is inherently hydrophobic. Bicomponent crimped fibers are formed incorporating this wettable resin. The fibers comprise a polypropylene portion and a portion which is formed of the wettable resin mixed with LLDPE (linear, low density polyethylene). At least the latter portion has at least part of its surface exposed to the exterior of the fiber. The fibers are thus rendered permanently hydrophobic. The fibers are cut into staple fibers 6 mm in length, and the staple fibers are airlaid to form a resilient web of wholly synthetic, hydrophilic fibers. The fibers have a diameter of about 18 $\mu$m. The process of airlaying includes the step of applying heat or an adhesive to cause those fibers which touch, or almost touch, one another to bond to each other and those points. Preferably, at least the major part of the fibers of the secondary sheet are the bicomponent fibers, and more preferably substantially 100% are, and most preferably 100% are.

The properties of the secondary sheet thus formed, using 100% bicomponent fibers, and using thermal bonding, are given in the following table under the heading Element 2. By way of comparison, the second column gives the properties of a secondary sheet used in an existing product sold for light incontinence by Kimberly Clark Corporation under the name Poise Pads R.A. For the purpose of the comparison test, a secondary sheet was removed from a Poise pad.

|  | Element 2 | Poise Pad R.A. 2nd Sheet |
| --- | --- | --- |
| Basis Weight (g/m$^2$) | 60 | 130 |
| Caliper (mm @ 2 kPa pressure) | 2.3 | 1.6 |
| Bulkiness (cc/g) @ 2 kPa pressure) | 38.3 | 12.3 |
| Dunk capacity (g/g/ @ P = 0) | 36.5 | 20.6 |
| Fluid Retention (g/g) | 0.01 | 1.5 |
| Fluid % discharge* | 99.97 | 92.72 |
| Wet Collapse (% loss @ 2.7 kPa) | 37.1 | 48.7 |
| Wet Resilience (% loss @ 0.1 kPa) | 17.7 | 42.5 |
| Wetting Time (sec) | 0.2 | 7.2 |

*Fluid % discharge = (Dunk capacity − Fluid Retention)/Dunk capacity × 100.

The table above demonstrates the superiority of the secondary sheet used in the invention in each of a number of important performance areas.

The high bulkiness demonstrates that it has a high void volume, and has the ability to acquire fluid efficiently.

The wetting time demonstrates the wettability of the web.

The low fluid retention value demonstrates the ability of the secondary sheet to drain the fluid almost completely (give up fluid into the storage core beneath it), so that the secondary sheet drains completely into the storage core and is therefore available for subsequent loadings.

The low wet collapse and low wet resilience values show that neither the capillary forces of fluid inside the structure, nor external pressure loadings, cause a harmful loss of the open void volume required for the structure to perform well.

The dunk capacity describes the property of being filled substantially totally with urine.

The storage core is a three-layer structure laminate, having the following layers:

a) A top layer having a weight of 75 g/m$^2$, of dry-formed, thermal-bonded, cellulose tissue with bicomponent polyolefin staple fibers. The latter are polyethylene-polypropylene ES-C fibers from Danaklon A/S, with a denier of 1.7 dtex and a length of 6 mm, the fibers consisting of polypropylene with a polyethylene sheath.

b) Middle layer of particulate (100–800 micron) polyacrylate AGM (absorbent gel material) Dow XZ type (200 g/m$^2$);

c) Bottom layer of air-laid, latex-bonded cellulose embossed tissue (55 g/m$^2$).

Alternatively, the structure may be made according to our Italian Patent Application No. TO 93 A 001028, which has similarities to what is described in TO 92 A 000566, but which incorporates an AGM material in a higher basis weight.

This structure is made according to Italian Patent Application TO 92 A 000566.

The backsheet is a 25 $\mu$m coextruded polypropylene/polyethylene film.

The dimensions and weights of Example 1 are set out in Table 1 below.

TABLE 1

| Material | Length (mm) | Width (mm) | Basis weight (g/m$^2$) | Grams/ pad | Surface/ pad (cm$^2$) |
| --- | --- | --- | --- | --- | --- |
| ABSORBENT CORE | 140 | 42 | 338 | 1.95 | 57.80 |
| Top Layer | 140 | 42 | 75 | 0.43 | |
| Middle Layer | 140 | 35 | 200 | 0.97 | |
| Bottom Layer | 140 | 42 | 55 | 0.32 | |
| TOPSHEET (partially perforated: 38 mm) | 153 | 67 (widest) 51 (narrowest) | 38 | 0.327 | 84.843 |
| SECONDARY SHEET | 140 | 40 | 60 | 0.347 | 57.80 |
| BACKSHEET | 153 | 67 (widest) 51 (narrowest) | 24 | 0.204 | 84.843 |
| Pad dimensions | 153 | 67 (widest) 51 (narrowest) | Pad weight: 3.38 g | | |
| Pad caliper | 3.1 mm @ 2 kPa 3.9 mm @ 0.2 kPa | | | | |

The absorbent pad of Example 1 is intended for use by someone suffering very light incontinence in which each fluid discharge averages about 5 ml and a gush rate of 15 ml/sec. The pad has an absorbent capacity in excess of 20 ml.

EXAMPLES 2 TO 4

These are largely identical to Example 1, except for differing dimensions and weights. These are set out in Tables 2 to 4 below which apply, respectively to Examples 2 to 4. However, as appears from Tables 3 and 4, in Examples 3 and 4 the absorbent core consists of five layers rather than three, to provide greater absorbent capacity. The top and bottom layers correspond to the top and bottom layers of Examples 1 and 2. The second and fourth layers are of an AGM material similar to the middle layer in Examples 1 and 2, and the third layer is of an airlaid, non-woven material identical to the bottom layer.

Example 2 is intended for someone for whom the average discharge is about 15 ml at a gush rate of 15 ml/sec. It has an absorbent capacity in excess of 40 ml. Example 3 is intended for someone for whom the average discharge is about 25 ml and at a gush rate of 20 ml/sec. It has an absorbent capacity in excess of 100 ml. Example 4 is intended for someone for whom the average discharge is about 50 ml and at a gush rate of 20 ml/sec. It has an absorbent capacity in excess of 150 ml. Examples 1 to 4 are sufficient between them to cover the needs of virtually all lightly or moderately incontinent women.

TABLE 2

| Material | Length (mm) | Width (mm) | Basis weight (g/m$^2$) | Grams/pad | Surface/pad (cm$^2$) |
|---|---|---|---|---|---|
| ABSORBENT CORE | 180 | 57 | 364 | 3.68 | 101.01 |
| Top Layer | 180 | 57 | 75 | 0.758 | |
| Middle Layer | 180 | 50 | 200 | 1.800 | |
| Bottom Layer | 180 | 57 | 55 | 0.556 | |
| TOPSHEET partially perforated: 44 mm | 210 | 90(widest) 75 (narrowest) | 38 | 0.619 | 160.70 |
| SECONDARY SHEET | 180 | 50 | 60 | 0.538 | 89.74 |
| BACKSHEET | 210 | 90(widest) 75 (narrowest) | 24 | 0.386 | 160.70 |
| Pad dimensions | 210 | 90(widest) 75 (narrowest) | Pad weight: 6.276 g | | |
| Pad caliper | 3.6 mm @ 2 kPa 4.1 mm @ 0.2 kPa | | | | |

TABLE 3

| Material | Length (mm) | Width (mm) | Basis weight (g/m$^2$) | Grams/pad | Surface/pad (cm$^2$) |
|---|---|---|---|---|---|
| ABSORBENT CORE | 216 | 54 | 560 | 6.562 | 116.64 |
| Top Layer | 216 | 54 | 75 | 0.875 | |
| Second Layer | 216 | 46 | 150 | 1.490 | |
| Third Layer | 216 | 54 | 55 | 0.642 | |
| Fourth Layer | 216 | 46 | 215 | 2.136 | |
| Bottom Layer | 216 | 54 | 55 | 0.642 | |
| TOPSHEET (partially perforated: 54 mm) | 252 | 102 (widest) 78 (narrowest) | 38 | 0.822 | 216.39 |
| SECONDARY SHEET | 234 | 84 (widest) 60 (narrowest) | 90 | 1.438 | 159.77 |
| BACKSHEET | 252 | 102 (widest) 78 (narrowest) | 24 | 0.519 | 216.39 |
| Pad dimensions | 252 | 102 (widest) 78 (narrowest) | Pad weight: 10.19 g | | |
| Pad caliper | 5 mm @ 2 kPa | | | | |

TABLE 4

| Material | Length (mm) | Width (mm) | Basis weight (g/m$^2$) | Grams/pad | Surface/pad (cm$^2$) |
|---|---|---|---|---|---|
| ABSORBENT CORE | 260 | 65 | 560 | 9.456 | 169.00 |
| Top Layer | 260 | 65 | 75 | 1.267 | |
| Second Layer | 260 | 57 | 150 | 2.223 | |
| Third Layer | 260 | 65 | 55 | 0.929 | |
| Fourth Layer | 260 | 57 | 205 | 3.038 | |
| Bottom Layer | 260 | 65 | 55 | 0.929 | |
| TOPSHEET (partially perforated: 54 mm) | 301 | 122 (widest) 93 (narrowest) | 38 | 1.173 | 308.68 |
| SECONDARY SHEET | 283 | 104 (widest) 75 (narrowest) | 130 | 3.126 | 240.5 |
| BACKSHEET | 301 | 122 (widest) 93 (narrowest) | 24 | 0.741 | 308.68 |
| Pad dimensions | 301 | 122 (widest) 93 (narrowest) | Pad weight: 15.51 g | | |
| Pad caliper | 7 mm @ 2 kPa | | | | |

The performance of Examples 1 and 2 versus existing products was evaluated in an acquisition test and a rewetting test. The way in which these tests are carried out is set out below, and the results are given in Tables 5 and 6.

TABLE 5

| Product | Thick (mm) | Core Fibers (g) | Composition AGM (g) | Theoretical Capacity (cc) | Acquisition Time (sec) 1st | 2nd | 3rd | Rewetting (g) |
|---|---|---|---|---|---|---|---|---|
| Always Ultra Normal | 4 | 1.7 | 0.8 | 29 | 6 | 22 | 28 | 0.0 |
| Poise Pad R.A. | 17 | 9.7 | 2.4 | 106 | 3 | 23 | 42 | 0.5 |
| Carefree | 3 | 1.5 | | 6 | 6 | 18 | Leaked | Leaked |
| Example 1 | 3.1 | 0.7 | 1.0 | 31 | 4 | 7 | 9 | 0.6 |

TABLE 6

| Product | Thick (mm) | Core Fibers (g) | Composition AGM (g) | Theoretical Capacity (cc) | Acquisition Time (sec) 1st | 2nd | 3rd | Rewetting (g) |
|---|---|---|---|---|---|---|---|---|
| Always Ultra Normal | 4 | 1.7 | 0.8 | 29 | 10 | 59 | Leaked | Leaked |
| Poise Pad R.A. | 17 | 9.7 | 2.4 | 106 | 4 | 41 | 49 | 0.1 |
| Poise Pad E.A. | 17 | 10.5 | 4.5 | 168 | 4 | 61 | 72 | 0.6 |
| Serene 10 cc (Kobayashi) | 5–12 Min-Max | 4.4 | 0.7 | 37 | 8 | 33 | Leaked | Leaked |
| Example 2 | 3.6 | 1.3 | 2.0 | 61 | 7 | 14 | 16 | 1.3 |

In the test of Table 5 there are 3 loadings each of 7 ml of fluid (21 ml total) at a rate of 20 ml/second. In Table 6 there are 3 loadings of 15 ml (45 ml total) at a rate of 20 ml/second. The word "leaked" indicates that because of leakage from the product a meaningful rewet value could not be obtained. CAREFREE is a Trade Mark used for pantiliners. ALWAYS ULTRA NORMAL is a Trade Mark used for catamenial pads. POISE PAD R.A., POISE PAD E.A. and SERENA are Trade Marks used for light incontinence products. Under the heading "CORE COMPOSITION", the term "fibers" denotes the weight of the cellulose-based part of the core and the term "AGM" denotes the weight of the absorbent gel material. The theoretical capacity is calculated as Fiber weight×4+AGM weight×28.

Some of the results of Tables 5 and 6, together with some additional results, are presented below in Table 7 in a somewhat different form. This shows the following values:

| | |
|---|---|
| t (mm): | thickness of article when dry, under a pressure of 20 g/cm². |
| s (ml): | theoretical fluid capacity of the article. |
| G (ml): | total volume of fluid applied to the article in three equal gushes separated by 10 minute intervals. |
| time (sec): | total of the three times taken for the three gushes to be absorbed. |
| g/t: | gush absorbance rate per mm thickness, where the gush absorbent rate g = G (ml)/time (sec). |

TABLE 7

| | t (mm) | s (ml) | s/t | G (ml) | time (sec) | g/t |
|---|---|---|---|---|---|---|
| Example 1 | 3.1 | 31 | 10 | 21 | 20 | 0.339 |
| Carefree | 3 | 6 | 2 | 21 | leaks | — |
| Always Ultra Normal | 4 | 29 | 7.2 | 21 | 56 | 0.094 |
| Poise R.A. | 17 | 106 | 6.2 | 21 | 68 | 0.018 |
| Example 2 | 3.6 | 61 | 16.9 | 45 | 37 | 0.338 |
| Always Ultra Normal | 4 | 29 | 7.2 | 45 | leaks | — |
| Poise R.A. | 17 | 106 | 6.2 | 45 | 94 | 0.028 |
| Poise E.A. | 17 | 168 | 9.9 | 45 | 137 | 0.019 |
| Serena 10 cc | 5–12 | 37 | 4.35* | 45 | leaks | — |
| Example 3 | 5 | 118 | 23.6 | 100 | 38 | 0.526 |
| Example 4 | 7 | 156 | 22.3 | 150 | 25 | 0.857 |

*Calculated assuming an average thickness of 8.5 mm

It will be seen that the value of g/t is substantially greater for the Examples according to the invention than for the prior art comparisons, showing a much greater rapidity in absorbing fluid in relation to their thickness. Also the value of s/t is greater, showing a greater total ability to absorb in relation to their thickness. It will be observed that the tests were carried out using three different sizes of gush, having regard to the fact that the products being tested were of different sizes. It can be seen that there is a degree of comparability in the Tests, at least as regards the Examples according to the invention, in that for all of them the value of G/s lies in a range of from ⅔ to 1 (0.68 for Example 1, 0.74 for Example 2, 0.85 for Example 3 and 0.96 for Example 4).

Two further examples are set out in Tables 8 and 9 below. Both are intended for use by someone suffering very light incontinence in which each fluid discharge averages about 5 ml and a gush rate of 15 ml/sec. In each case the pad has an absorbent capacity in excess of 20 ml.

TABLE 8

| Material | Length (mm) | Width (mm) | Basic weight (p/m²) | Grams/pad | Surface/pad (cm²) |
|---|---|---|---|---|---|
| ABSORBENT CORE | 140 | 37 | 347 | 1.80 | 51.80 |
| Top Layer | 140 | 37 | 75 | 0.39 | |
| Middle Layer | 140 | 29 | 200 | 0.81 | |
| Bottom Layer | 140 | 37 | 55 | 0.28 | |
| TOPSHEET | 165 | 70 (widest) 55 (narrowest) | 38 | 0.377 | 99.317 |
| SECONDARY SHEET | 150 | 57 (widest) 42 (narrowest) | 60 | 0.428 | 71.270 |
| BACKSHEET | 165 | 70 (widest) 55 (narrowest) | 24 | 0.238 | 99.317 |
| Pad dimensions | 165 | 70 (widest) 55 (narrowest) | Pad weight: 3.523 g | | |
| Pad caliper | 3.1 mm @ 2 kPa 3.9 mm @ 0.2 kPa | | | | |

TABLE 9

| Material | Length (mm) | Width (mm) | Basic weight (p/m²) | Grams/pad | Surface/pad (cm²) |
|---|---|---|---|---|---|
| ABSORBENT CORE | 180 | 45 | 390 | 3.16 | 81.00 |
| Top Layer | 180 | 45 | 75 | | |

TABLE 9-continued

| Material | Length (mm) | Width (mm) | Basic weight (p/m²) | Grams/ pad | Surface/ pad (cm²) |
|---|---|---|---|---|---|
| Middle Layer | 180 | 37 | 220 | | |
| Bottom Layer | 180 | 45 | 55 | | |
| TOPSHEET (partially perforated: 44 mm) | 210 | 85 (widest) 65 (narrowest) | 38 | 0.572 | 150.51 |
| SECONDARY SHEET | 194 | 69 (widest) 51 (narrowest) | 60 | 0.667 | 111.09 |
| BACKSHEET | 210 | 85 (widest) 65 (narrowest) | 24 | 0.361 | 150.51 |
| Pad dimensions | 210 | 85 (widest) 65 (narrowest) | Pad weight: 5.654 g | | |
| Pad caliper | 3.6 mm @ 2 kPa 4.1 mm @ 0.2 kPa | | | | |

One variation of what is described above is to use two layers of the secondary topsheet material rather than one. These layers can be held together if required by a liquid-permeable adhesive layer.

The following sets out the methods used to measure various parameters mentioned above:

Dunk Capacity

This method evaluates the free absorption capacity of the material. A rectangular sample of material 25.4×100 mm is put onto the surface of a liquid (synthetic urine, of which the composition is given below) and left on it for one minute. It is then withdrawn by means of a metallic net and left to drip in horizontal position for one minute.

The dunk capacity is obtained as:

(Wet weight–dry weight)/dry weight of the sample (g/g).

Fluid Retention

The samples obtained from the above test method are rotated in a centrifuge under a g-force of 240 g for ten minutes.

The fluid retention is obtained as:

(Wet weight–dry weight)/dry weight of the sample (g/g).

Wet Collapse

The samples 38×50 mm are made of as many superimposed layers of material as are needed to get an overall basis weight of 500 g/m². The samples are wetted in the same was as in the dunk capacity test. They are then placed on a perforated plexiglass plate and subjected to three dynamic cycles of compression and decompression (speed of the pressing head 10 mm/min, maximum load for each cycle 2.7 kPa). The minimum thickness of the sample under compression is measured.

The wet collapse is:

(initial thickness–minimum thickness/initial thickness of the sample)×100(%).

Wet Resilience

In the above described test the final thickness of the sample after the last decompression is measured.

The wet resilience is then obtained as:

(initial thickness–final thickness)/(initial thickness)×100 (%).

Wetting Time

In this test, samples of the secondary sheet of the present invention and samples of the second sheet of Poise Pad R.A. having the same volume of about 5 cc are compared. The considered thicknesses correspond to the calipers under pressure (see the values on the table). The samples are placed horizontally onto the surface of water by means of a metallic net. The wetting time is the time needed for each sample to get completely soaked.

Acquisition Test

This method evaluates the time required for the acquisition of given amounts of liquid during repeated imbitions (three in this case), at a high speed (20 ml/sec) and under a low pressure (2.7 kPa).

Each product is laid down on a flat surface and an acquisition plate is placed on it. The acquisition plate comprises a rectangular plexiglass plate 70×220×8 mm with an aperture 22 mm in diameter formed therein. A cylinder 45 mm high and 22 mm in internal diameter is located over the aperture in sealing contact with the plate. The cylinder is filled with synthetic urine to which a dye has been added and a pressure of 2.7 kPa is applied to the plate, obtained with appropriate weights positioned on the plate, the pressure being that measured with reference to the portion of the product under the acquisition plate. The acquisition time is the time from the beginning of each imbition until the disappearance of the liquid from the interior of the cylinder. A waiting time of 10 minutes is left after each imbition before repeating the procedure.

Rewetting Test 10 minutes after the last imbition in the acquisition test the acquisition plate is removed and ten sheets of absorbent paper (220 g/m² each) are positioned over the product. A plexiglass plate (180×60 mm) is put onto the absorbent paper and the portion of the product under the plate is then subjected to a pressure of 5.9 kPa. The amount of liquid absorbed by the absorbent paper is taken as the rewetting value for each sample.

Composition of the Synthetic Urine Used in the Tests

The synthetic urine is a solution in distilled water containing the following salts (in weight percent):

Urea 2%, sodium chloride 0.9%, magnesium sulphate (heptahydrate) 0.11%, calcium chloride 0.06%.

What is claimed is:

1. An article for absorbing fluid, which comprises, successively from a first face thereof to an opposite face, a fluid-permeable topsheet (1), a fluid-receiving region (6), a fluid-storage region (7), and a fluid-impermeable backsheet (2), the fluid-receiving region being formed of a dry laid web of staple, permanently hydrophilic, synthetic fibers, the web having a bulkiness, as measured under a pressure of 2 kPa, of at least 15 cm³/g, and a thickness of from 1 to 10 mm, the fluid-receiving region being adapted to release to the fluid-storage region at least 99% of the fluid which it receives, wherein 100% of the fibers of the fluid-receiving region are bicomponent fibers, each fiber comprising a polypropylene portion, and a portion which has a surface exposed to the exterior of the fiber and which is formed of a polyethylene resin with a wetting agent incorporated therein.

2. An article according to claim 1, wherein the said bulkiness is not more than 65 cm³/g.

3. An article according to claim 2, wherein the said bulkiness is from 20 to 60 cm³/g.

4. An article according to claim 3, wherein the said bulkiness is from 25 to 55 cm³/g.

5. An article according to claim 4, wherein the said bulkiness is from 30 to 50 cm³/g.

6. An article according to claim 1, wherein the said thickness is from 1.5 to 6 mm.

7. An article according to claim 6, wherein the said thickness is from 1.7 to 4.5 mm.

8. An article according to claim 7, wherein the said thickness is from 2 to 4 mm.

9. An article according to claim 1, wherein the basis weight of the material of the said fluid-receiving region is from 25 to 300 g/m².

10. An article according to claim 9, wherein the said basis weight is from 40 to 200 g/m².

11. An article according to claim 10, wherein the said basis weight is from 50 to 180 g/m².

12. An article according to claim 1, wherein the material of the said fluid-receiving region has a wet collapse value of not more than 45%, as measured by the wet collapse test method described herein.

13. An article according to claim 12, wherein the said wet collapse value is not more than 40%.

14. An article according to claim 1, wherein the material of the said fluid-receiving region has a wet resilience value of not more than 40%, as measured by the wet resilience test method described herein.

15. An article according to claim 14, wherein the said wet resilience value is not more than 25%.

16. An article according to claim 15, wherein the said wet resilience value is not more than 25%.

17. An article according to claim 1, wherein the material of the said fluid-receiving region has a wetting time of not more than 5 seconds, as measured by the wetting time test method described herein.

18. An article according to claim 17, wherein the said wetting time is not more than 2 seconds.

19. An article according to claim 1, wherein the material of the fluid-receiving region is formed using fibers having a diameter not more than 40 μm.

20. An article according to claim 19, wherein the said diameter is from 15 to 20 μm.

21. An article according to claim 1, wherein the said fluid-storage region comprises an absorbent hydrogel material.

22. An article according to claim 21, wherein the said fluid-storage region further comprises a cellulose material.

23. An article according to claim 21, wherein the said absorbent hydrogel material is in particulate form.

24. An article according to claim 1, wherein the said fluid-storage region comprises a laminate having outer layers of cellulose-containing material and an intermediate layer of absorbent hydrogel material.

25. An article according to claim 1, wherein the said fluid-storage region comprises a laminate having outer layers and a central layer of cellulose-containing material, and two further layers of absorbent hydrogel material respectively between the central layer and the two outer layers.

26. An article according to claim 1, wherein the said fluid-receiving region is in the form of a sheet, and the said fluid-storage region is in the form of a further sheet in face-to-face relationship with the fluid-receiving sheet.

27. An article according to claim 26, wherein the said fluid-receiving sheet and the said fluid-storage sheet are secured to one another by an adhesive.

28. An article according to claim 1, wherein the topsheet and backsheet are sealed to one another around the periphery thereof.

29. An article according to claim 28, the article having a thickness, when dry of $t_d$, and a thickness, when wetted to its maximum extent, of $t_w$, with $t_w > t_d$, the topsheet and backsheet being sealed together along respective edge portions thereof, and the topsheet having a fluid permeable central area, and a fluid impermeable area adjacent the sealed edge portion thereof, the size of the fluid impermeable area being such that, even when the article is wet to its maximum extent, the fluid permeable area of the sheet is not in communication with at least a major portion of the edges of the fluid-receiving sheet.

30. An article according to claim 1, shaped to form a pad suitable for incontinent females.

31. An article according to claim 1, in the form of an absorbent pad for use by a user suffering from incontinence, the pad having a thickness when dry of t mm, as measured with the pad under pressure of 2 kPa, a fluid storage capacity of s ml and the ability to receive gushes at an average rate, as measured over three successive equal gushes totalling G (ml), of up to g ml/sec, where $s/t \geq 8$ ml/mm; and $g/t \geq 0.1$ ml/mm. sec at least for some value of $G/s \geq 2/3$.

32. An article according to claim 31, wherein $g/t \geq 0.2$ ml/mm. sec.

33. An article according to claim 32, wherein $g/t \geq 0.3$ ml/mm. sec.

* * * * *